United States Patent [19]

Summ

[11] Patent Number: 4,658,409
[45] Date of Patent: Apr. 14, 1987

[54] COMPRESSION DEVICE FOR AN X-RAY DIAGNOSTIC APPARATUS

[75] Inventor: Herbert Summ, Wilhelmsdorf, Fed. Rep. of Germany

[73] Assignee: Siemens Aktiengesellschaft, Berlin and Munich, Fed. Rep. of Germany

[21] Appl. No.: 666,246

[22] Filed: Oct. 29, 1984

[30] Foreign Application Priority Data

Nov. 4, 1983 [DE] Fed. Rep. of Germany ....... 3340019

[51] Int. Cl.$^4$ ............................ A61B 6/04; H05G 1/00
[52] U.S. Cl. ...................................... 378/37; 378/117; 378/204
[58] Field of Search ................ 378/37, 204, 208, 207, 378/117; 250/491.1

[56] References Cited

U.S. PATENT DOCUMENTS

| | | | |
|---|---|---|---|
| 3,609,355 | 9/1971 | Schwarzer | 378/37 |
| 4,259,585 | 3/1981 | Novak et al. | 378/37 |
| 4,573,180 | 2/1986 | Summ | 378/195 |

FOREIGN PATENT DOCUMENTS

| | | |
|---|---|---|
| 1942490 | 8/1969 | Fed. Rep. of Germany . |
| 2356276 | 7/1974 | Fed. Rep. of Germany . |
| 1041424 | 9/1966 | United Kingdom . |

OTHER PUBLICATIONS

Siemens Brochure "MAMMOMAT B", M-R 87/7318, dated Jan., 1982.

Primary Examiner—Janice A. Howell

[57] ABSTRACT

In an exemplary embodiment a compression carriage, adjustable by means of an electromotor, supports a compression localizer with which a switch is associated which disconnects the motor when the compression localizer engages the radiography subject. The connection between the motor and compression localizer can be selectively disengaged manually so as to allow manual movement of the compression localizer while the motor remains deenergized.

2 Claims, 5 Drawing Figures

COMPRESSION DEVICE FOR AN X-RAY DIAGNOSTIC APPARATUS

BACKGROUND OF THE INVENTION

The invention relates to a compression device for an X-ray diagnostic apparatus, comprising a compression carriage which is adjustable by means of an electromotor, said compression carriage supporting a compression localizer with which switching means are associated which disconnect the motor when the compression localizer engages the radiography subject.

An X-ray diagnostic apparatus comprising a compression carriage of this type is known which serves the purpose of preparation of radiographs of the human female breast. The radiography subject is placed on a radiographic plate and subsequently compressed by motor means. The motor for the compression carriage is automatically disconnected by spring-loaded switching means when the force on the radiography subject attains a predetermined value.

In the case of the known compression device, a sudden, i.e. not a sensitive, disconnection of the motor for the compression device takes place. As a consequence of the inertia of the moved parts it is possible for the force on the radiography subject to further increase in an undesired manner after the disconnection of the motor.

From the German OS No. 2,356,276, it is already known in the case of an X-ray spot film device to switch over the speed of the drive motor in a stepwise fashion in dependence upon the force acting on the patient.

SUMMARY OF THE INVENTION

The object underlying the invention resides in designing a compression device of the initially cited type such that the pressure of the compression localizer on the radiography subject can be released manually In accordance with the invention, this object is achieved by virtue of the fact that means are present for releasing the connection between the motor and the compression localizer. In the case of the inventive compression device, it is possible to manually disconnect the motor from the compression localizer and hence to manually release the compression localizer from the radiography subject.

Expedient embodiments of the invention are apparent from the subclaims in conjunction with exemplary embodiments illustrated on the accompanying drawing sheets; and other objects, features and advantages will be apparent from this detailed disclosure and from the appended claims.

DETAILED DESCRIPTION

Figure 1:
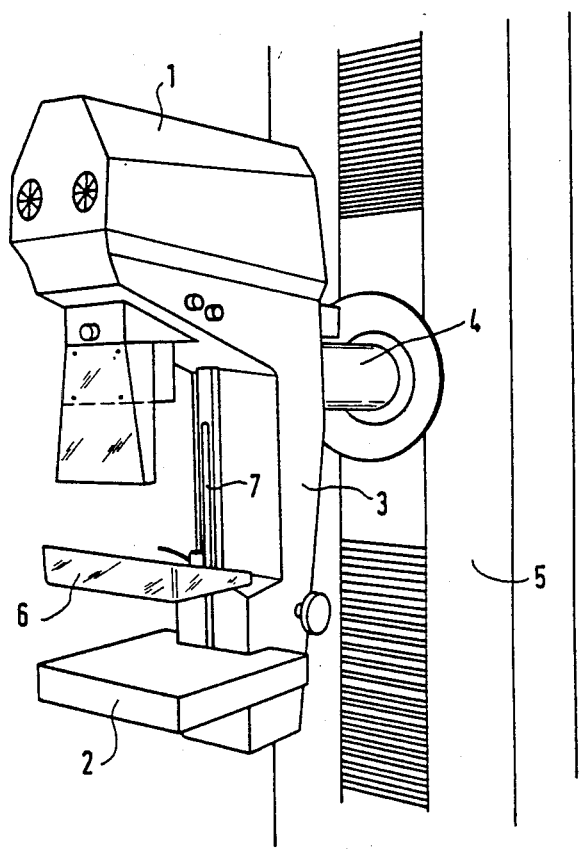
FIG. 1 shows an X-ray diagnostic apparatus comprising a compression device, for explaining the inventive concept.

In FIG. 1, an X-ray diagnostic apparatus for taking mammograms is illustrated wherein a housing 1 contains an X-ray tube, and a radiographic plate 2 is provided for receiving a radiography subject. The components 1, 2 are arranged on a support 3 which, with the aid of a shaft 4, is mounted on a stand 5. Relative to this stand 5, the support 3 is rotationally adjustable about the axis of shaft 4, and is also adjustable in height above a floor surface on which the stand 5 is mounted.

For the compression of the radiography subject a compression device with a compression localizer 6 is provided which is height-adjustable with a non-illustrated attachment arm which moves in a slot 7 of the support 3. The attachment arm of the compression localizer 6 is coupled with a compression carriage to be explained in further detail in the following description of FIG. 2. The compression localizer 6 is moved toward and away from radiographic plate 2 by means of an electromotor. In this manner, the compression localizer 6 can be pressed from above against the radiography subject, disposed on the radiographic plate 2, and can compress the radiograph subject to a desired extent.

Figure 2:
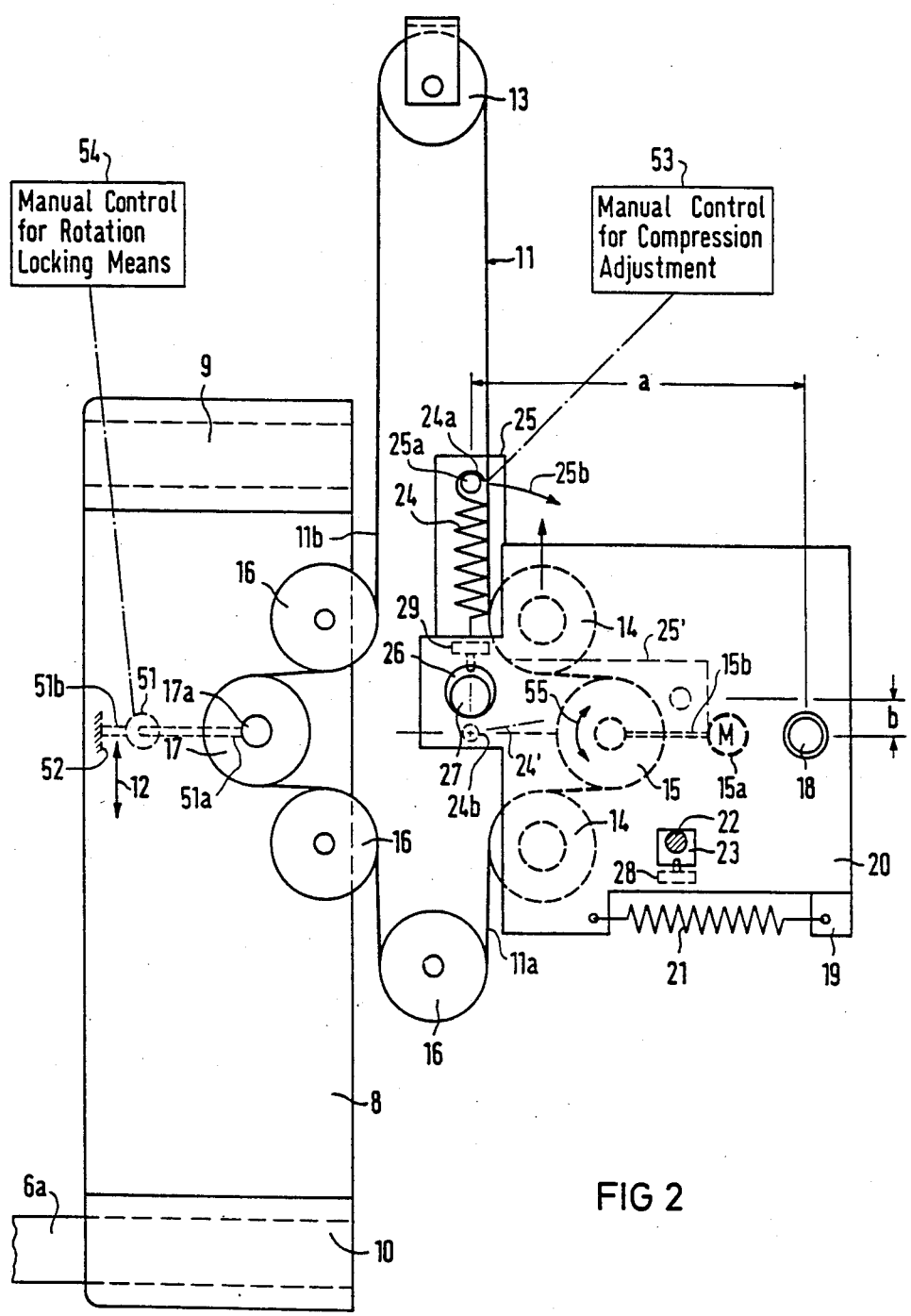
FIG. 2 shows details of the X-ray diagnostic apparatus according to FIG. 1.

FIG. 2 shows the compression carriage 8 with two openings 9, 10, for selectively receiving the attachment arm 6a of the compression localizer 6. By way of example, arm 6a and openings 9 and 10 may be of rectangular cross section. The compression localizer 6 is inserted in the opening 10 as indicated in FIG. 2 when radiographs are to be prepared in the described fashion. If the radiograph is to be prepared with the use of enlarging technique, the compression localizer 6 is inserted in the opening 9 and, between the radiographic plate 2 and the compression localizer 6, a supporting plate is mounted on the support 3 at a distance above the radiographic plate 2. In this case, one then obtains enlarged radiographs.

The compression carriage 8 is adjusted by means of a toothed belt 11 in a vertical direction as indicated by the double arrow 12. The belt 11 is guided by a tension roller 13, two rollers 14, a drive roller 15, guide rollers 16, and a coupling roller 17. The drive roller 15 is driven by motor means 15a. Two plates 19, 20 are pivotally mounted in spaced parallel relation on a shaft 18 which is fixedly mounted by support 3. The plate 19 mounts the rollers 14 at their rear sides remote from the plate 20. The rollers 14 are clear of plate 20 at the front sides thereof. The roller 15 is mounted between plates 19 and 20, with clearance therefrom, so as not to interfere with the pivotal movement of plates 19, 20 on the shaft 18. The tension spring 21 causes the plate 19 to be urged in a clockwise direction about shaft 18, so that a pin 22 on the plate 19 is pressed against the upper edge of an opening 23 in plate 20. By means of a stronger tension spring 24 which engages at end 24a with a pin 25a on a lever 25, on the one hand, and is secured at its opposite end 24b to the plate 20, on the other hand, the plate 20 is urged in a clockwise direction about shaft 18 so that the underside of an opening 26 of plate 20 abuts against a limit stop 27 which is fixed relative to support 3.

In order to adjust the compression carriage 8 in a vertical direction, the shaft 17a of coupling roller 17 is locked against rotation so that, upon rotation of the drive roller 15, an upward movement, or downward movement respectively, of the compression carriage 8 takes place. The upward movement always proceeds with the same speed. The downward movement first proceeds with a high speed until the compression localizer 6, FIG. 1, carried by arm 6a rests against the radiography subject. Due to the occurring resistance, the tension at region 11a of the toothed belt 11 increases and the rollers 14 move, together with the plate 19, about the shaft 18 in a counterclockwise direction. The spring 21 is, thus, tensioned. If, with this movement of plate 19 and pin 22 carried thereby, the pin 22 reaches the lower edge of the opening 23, it actuates a microswitch 28 mounted on the plate 20 and thereby causes the drive motor 15a and thus the compression carriage 8 to be switched over to a lower speed.

With the further movement of the compression localizer and hence also of the compression carriage 8, the plate 19 with the limit pin 22, further swivels by means of the rollers 14 in a counterclockwise direction, and now entrains the plate 20 by engagement of pin 22 at the lower side of the opening 23 so that also the plate 20 is swiveled in a counterclockwise direction about shaft 18, such that the spring 24, which is stronger than the spring 21, is tensioned. The opening 26 thus moves relative to the shaft 27 (which is fixedly mounted on support 3) until the shaft 27 strikes a microswitch 29 mounted on plate 20 at the upper side of the opening 26 and shuts down the drive motor 15a.

The spring 24, together with the lever 25 on the shaft 27, is capable of being swiveled in a clockwise direction as indicated by arrow 25b. With this swivel movement, the effective lever arm relative to shaft 18 becomes smaller. In FIG. 2, for example, a large lever arm a and a small lever arm b for the spring force are illustrated. Accordingly, through swivelling of the lever 25, the force at which the end shutoff of the drive motor 15a takes place, is adjustable.

If the compression localizer 6 with the compression carriage 8 is to be manually adjusted, a coupling 51 between the shaft 17a and a region 52 of the carriage 8 can be released manually by a manual control 54 so that the coupling roller 17 can freely rotate along with its shaft 17a. The motor 15a locks the drive roller 15 against rotation so that as the carriage 8 is moved manually, rollers 16 and 17 roll along the run 11b of the belt 11.

Figure 3:
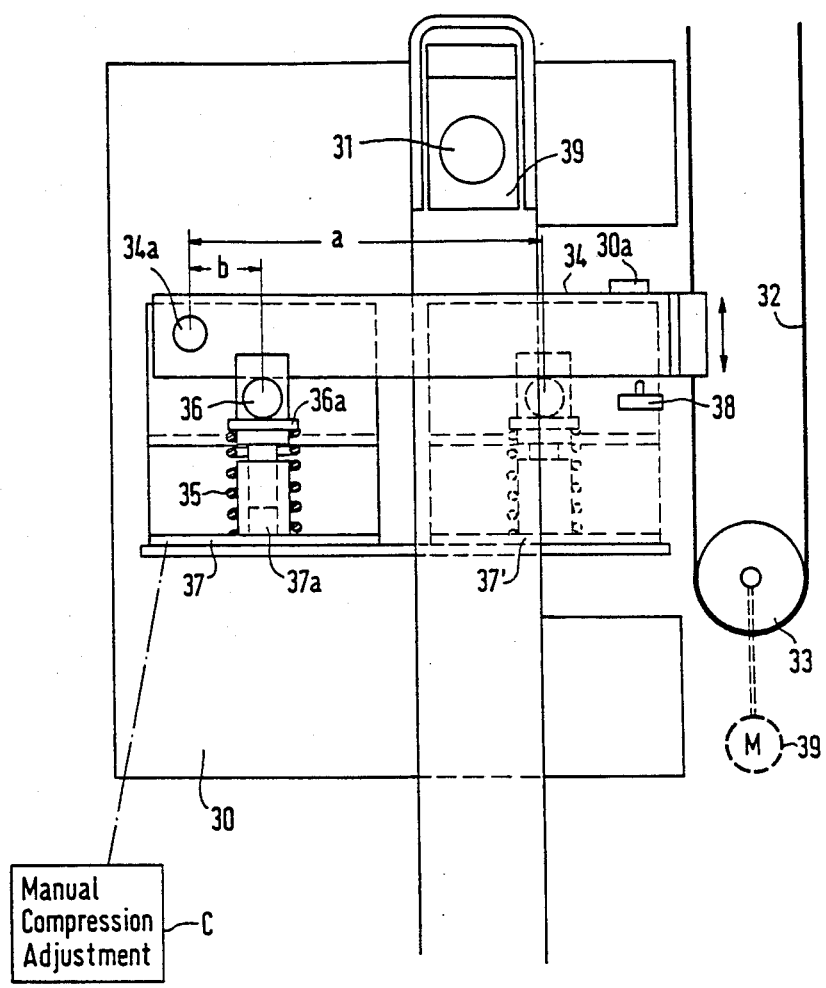
FIG. 3 shows a variant of the arrangement according to FIG. 2.

The exemplary embodiment according to FIG. 3, shows the compression carriage 30 which, in contrast to the compression carriage 8 in FIG. 2, is shown in a view from the front. An upper opening 31 serves the purpose of accommodating the compression localizer 6 for the preparation of a radiograph in enlargement technique. Corresponding to FIG. 2, a non-illustrated, loweropening for normal radiographs is also provided. Serving the purpose of adjustment of the compression carriage 30, is a toothed belt 32 which is guided via a drive roller 33 and is secured to a lever 34 which is pivotal about a shaft 34a on the compression carriage 30.

The lever 34 is pressed by means of a compression spring 35 against a limit stop 30a on carriage 30, said spring 35 pressing an abutment lug 36 against the lower edge of the lever 34. The compression spring 35 encircles a guide post 37a of a spring carriage 37 and acts on a flange 36a associated with lug 36 at its upper end. The spring carriage 37 is adjustable in a horizontal direction on the compression carriage 30 in non-illustrated guides by means of a manually adjustable control indicated at C. The vertical position of carriage 37 on the compression carriage 30, by contrast, is not alterable.

If the compression localizer strikes the radiography subject the toothed belt 32, with the right end of the lever 34, moves further downwardly against the action of spring 35 until it strikes a microswitch 38 and shuts down the motor 39. The force at which the motor 39 which drives the roller 33 is shut down is adjustable by means of horizontal displacement of the spring carriage 37. In the position of the spring carriage 37 shown in dot dash lines at 37' this force is greater than in the position illustrated in solid lines.

Figure 4:
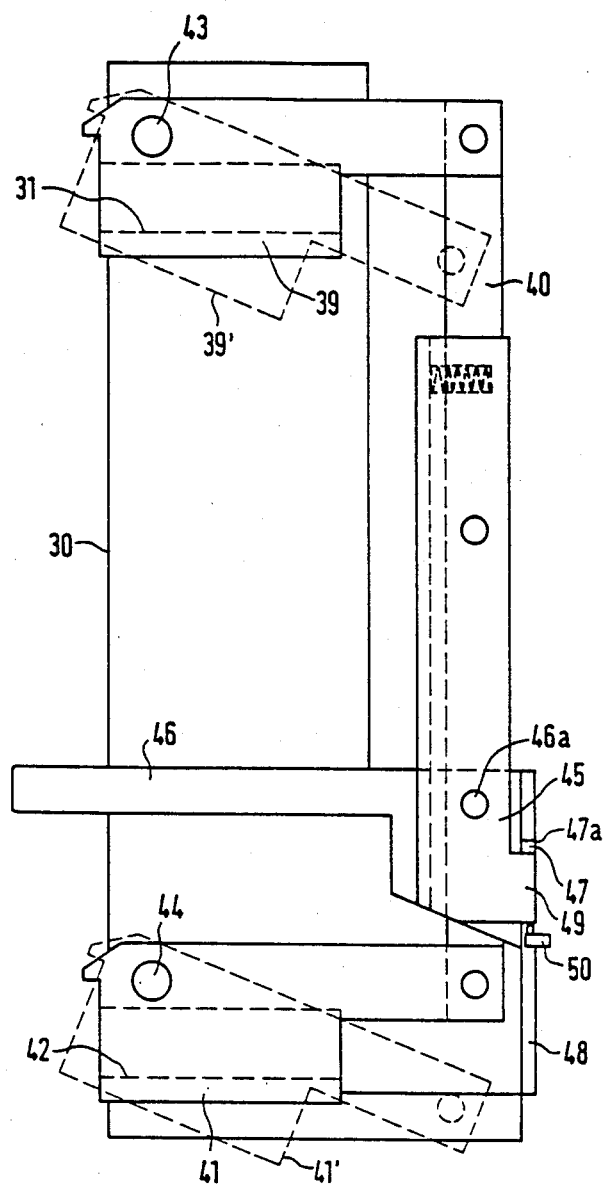
FIGS. 4 and 4A show the variant according to FIG. 3 in a different view.

The switching over of the drive motor 39 to a lower speed is explained in greater detail in conjunction with FIG. 4 which shows the compression carriage 30 in a lateral view. From FIG. 4, it is apparent that the opening 31 is formed by a sleeve 39 which, via a bar 40, is connected in an articulated fashion with a sleeve 41, disposed therebelow, with an opening 42. The opening 42 of sleeve 41 serves the purpose of accommodating the compression localizer 6 for normal radiographs. The sleeves 39 and 41 are pivotal about axes 43 and 44. A locking bar 45 is adjustably mounted on the bar 40, which bar, with the aid of a lever 46, is capable of being moved out of an opening 47 of a stop plate 48.

In the position of the sleeves 39, 41 illustrated in solid lines, the limit stop 49 of the bar 45 is disposed in the opening 47. It is so designed that a clearance is present between the limit stop 49 and the top edge 47a of the opening 47. Due to the localizer weight and the spring force, the limit stop 49 is pressed against the upper edge 47a of the opening 47 when the localizer 6 does not yet rest against the radiography subject. When it reaches the radiography subject, the sleeves 39, 41 are very slightly swiveled in a clockwise direction and the limit stop 49 moves into a lower position as viewed in FIG. 4 in which it actuates a microswitch 50 and switches the motor 39 to a lower speed.

The lever 46 serves the purpose of manual release of the radiography subject. If the lever 46 is moved about the shaft 46a in a clockwise direction, it draws the limit stop 49 out of the opening 47 so that the sleeves 39, 41, can be manually positioned in the position illustrated in broken lines at 39', 41' in which the localizer 6 is disposed above its end position and releases the radiography subject.

It will be apparent that many modifications and variations may be made without departing from the scope of the teachings and concepts of the present invention.

SUPPLEMENTARY DISCUSSION

Referring to FIG. 2, the drive couplings between motor means 15a and drive roller 15, and between coupling roller 17 and locking means 51, have been indicated in an entirely diagrammatic manner. By way of example motor means 15a including its output gearing may be mounted on support 3, at the rear side of plate 19 (the rear side of plate 19 being the side more remote from plate 20), and the gearing may include an output shaft 15b to which drive roller 15 is secured, the drive roller 15 being located between plates 19 and 20, and the shaft 15b actually extending along the axis of rotation of drive roller 15 and through a suitable arcuate slot in plate 19. Similarly, shaft 51a of coupling 51 may extend along the axis of rotation of coupling roller 17 and be fixedly secured to or integral with shaft 17a so as to rotate jointly with shaft 17a and coupling roller 17 at all times. The shaft 51b of coupling 51 is secured against rotation as indicated at 52, e.g. by being secured to the compression carriage 8.

When a drive coupling between drive roller 15 and the compression carriage 8 is to be effected, the shaft 51a is mechanically positively engaged with the shaft 51b by means of manual control of coupling 51 to its engaged condition. If later, with the compression localizer 6 stopped in its pressure applying position, it is desired to manually release the compression carriage 8 so that it can be manually raised, the coupling 51 is manually released so that coupling roller 17 with the associated shafts 17a, 51a is free to rotate. Thus, even though belt 11 is fixed against longitudinal movement by the de-energized state of motor 15a with its gearing, the rollers 16, 17 can move upwardly along run 11b of the belt 11 as the compression carriage is manually raised.

By way of example, coupling 51 may take the form of a manually controlled positive clutch mechanism which in its engaged position locks shaft 51a against rotation in both directions, while when disengaged, permits shaft 51a to rotate freely relative to shaft 51b. An elementary form of such a positive clutch with manually operated means for effecting engagement and disengagement is shown in the first figure at page 224 of volume three of McGraw-Hill Encyclopedia of Science and Technology, 1960. The clutch jaws may have intermeshing pointed teeth so as to be readily engaged in any relative angular position. If desired the pointed teeth may have rectilinearly disposed flanks for positive driving engagement with the cooperating flanks of the opposing teeth essentially as shown in the first figure at page 224 of the above-referenced volume three.

In reference to said figure one at page 224, the through shaft may correspond with shaft 51a, and parts 51b, 52 may be formed by the right hand clutch part which would be fixedly mounted on carriage 8. The right hand end of the through shaft would correspond with shaft 17a and carry coupling roller 17. The shaft portion corresponding to 51a would be splined to accommodate axial shifting of the left hand clutch part into engagement with the right hand clutch part, and the operating lever could be accessible for manual operation at the left side of support or housing 3, FIG. 1.

For the sake of diagrammatic indication, a manual control for the compression adjustment lever 25 is indicated at 53 in FIG. 2, and a manual control for the rotation locking means 51 is indicated at 54. The control 53 may be of the infinitely adjustable (analog or continuous) type and may be frictionally held in any angular position of lever 25 between the solid line position (maximum compression) and the dot dash line position 25' (minimum compression).

The manual control 54 may be a toggle type control with one position corresponding to locking of coupling roller 17 against rotation, and a second position allowing free rotation of coupling roller 17.

By way of example, lever 25 may be pivotal about the axis of limit stop pin 27, FIG. 2, which may be secured to the housing or support 3.

The motor means 15a may include worm gearing or the like such that drive roller 15 is locked against rotation when the electric motor of means 15a is deenergized. The motor means 15a may be reversible as indicated by double arrow 55, e.g. by means of a reversible electric motor.

Figure 4A:
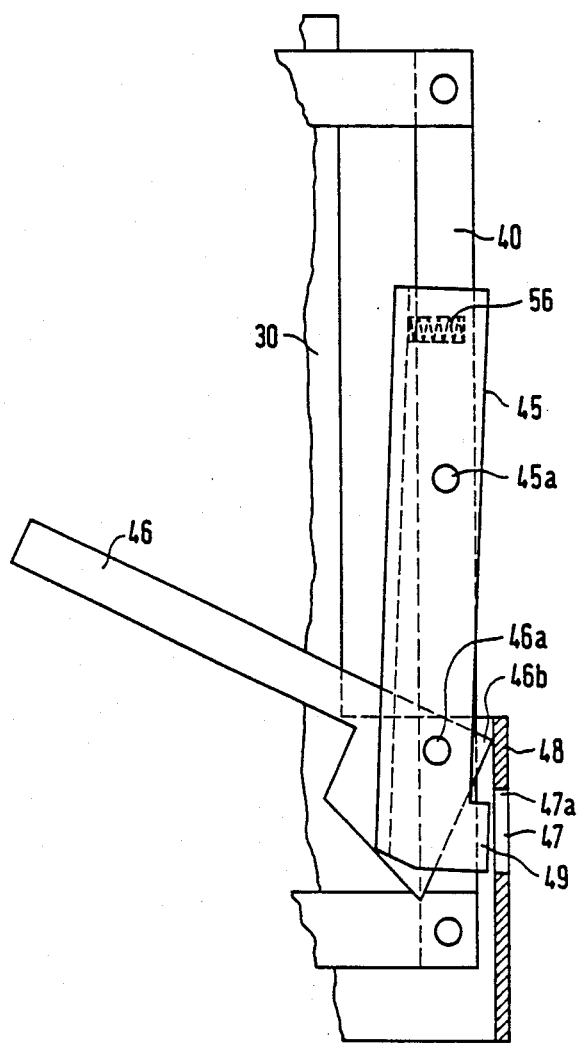

FIG. 4A shows the parts of FIG. 4 in a release position of lever 46. It will be observed that manual pivoting of lever 46 about pivot 46a engages lever edge 46b with stop plate 48, to shift bar 45 in a clockwise direction about its pivot point 45a against the action of compression spring 56, so as to release limit stop 49 from opening 47 and allow the components 39, 40, 41, FIG. 4, to move to the release position (indicated at 39' and 41' in FIG. 4).

By way of background to the present invention, reference may be made to the brochure of Siemens AG entitled "MAMMOMAT B", PIR 87-022, M-R 87/7318, dated January 1982, showing a diagnostic installation including parts corresponding to parts 1, 2, 3, 4, 5 and 6 of FIG. 1. In this prior system, the compression motion is controlled with the assistance of a foot pedal. The maximally exertable pressure can be set from 80N (8 kilopond) through 150N (15 kilopond) during assembly, and a corresponding range of stopping pressures can be selected by the continuous type manual adjustment means 53 in FIG. 2 of the present disclosure, and by the continuous type manual adjustment means C of FIG. 3 hereof. The housing 3, FIG. 1, may pivot on the axis of shaft 4 through a range of twelve angular degrees, for example.

From the foregoing conventional expression of pressures in terms of force units (newtons) with the area units understood, it can be seen that the pressure adjustment can be selected by the means 53, FIG. 2, or C, FIG. 3, at any desired value over a range of pressures where the maximum selectable pressure is at least twice the minimum selectable pressure. More particularly, FIG. 2 of the present disclosure shows a ratio of maximum stopping pressure to minimum stopping pressure (a/b) of at least about nine to one, while FIG. 3 shows a corresponding ratio (a/b) of at least four to one.

I claim as my invention:

1. A compression system for an X-ray diagnostic apparatus, comprising, a compression carriage movable along a predetermined path and having a compression localizer coupled therewith for movement into engagement with a radiaography subject, a motor for driving said compression carriage along the predetermined path to effect engagement of the compression localizer with the radiography subject, switch means controlling said motor and responsive to engagement of the compression localizer with the radiography subject to deactivate said motor, disengagement means providing a selectively a disengageable coupling between said motor and said compression localizer to disconnect said compression carriage from said motor, and manually actuatable control means connected to said disengagement means and manually actuatable to release said disengageable coupling to allow free movement of said compression carriage relative to said radiography subject and independently of whether said motor is running or is stopped.

2. A compression system according to claim 1, with said compression carriage has a carrier means mounted on the compression carriage on a pivot axis such that the compression localizer is released from engagement with a radiography subject when said carrier rotates, and said disengagement means comprising a locking device interposed between said carriage and said carrier means for selectively locking said carrier means against rotation, and said locking means being selectively manually releasable to allow manual movement of said compression localizer while the carriage remains in a fixed position and whether said motor is running or is stopped.

* * * * *